United States Patent [19]

Iyer et al.

[11] Patent Number: 5,376,306
[45] Date of Patent: Dec. 27, 1994

[54] POLYMERIC BUFFERING COMPOSITION

[75] Inventors: Lokanathan M. Iyer, Edmonds; Kenneth S. Lyon, Everett; Vince Brotherton, Seattle, all of Wash.

[73] Assignee: Abbott Laboratories, Abbott Park, Ill.

[21] Appl. No.: 149,659

[22] Filed: Nov. 5, 1993

Related U.S. Application Data

[62] Division of Ser. No. 813,276, Dec. 23, 1991, Pat. No. 5,298,645.

[51] Int. Cl.$^5$ .................... G01N 31/22; C08F 226/00; C08F 220/10
[52] U.S. Cl. .................... 252/408.1; 526/312; 526/328.5
[58] Field of Search .................... 526/312, 328.5, 408.1

[56] References Cited

U.S. PATENT DOCUMENTS

| | | | |
|---|---|---|---|
| 4,434,249 | 2/1984 | Ballestrasse et al. | 521/27 |
| 4,910,325 | 3/1990 | Shen et al. | 558/260 |
| 4,925,268 | 5/1990 | Iyer et al. | 350/96.29 |
| 4,973,303 | 11/1990 | Johnson et al. | 604/20 |
| 5,000,901 | 3/1991 | Iyer et al. | 264/299 |

OTHER PUBLICATIONS

Holum, John R., "Elements of General and Biological Chemistry", John Wiley and Sons, Inc., pp. 136–137 (1965).

*Primary Examiner*—Joseph L. Schofer
*Assistant Examiner*—Wu C. Cheng
*Attorney, Agent, or Firm*—Christensen, O'Connor, Johnson & Kindness

[57] ABSTRACT

High molecular weight buffering compositions and polymeric buffering compositions incorporating such compositions are described. The compositions are useful in applications where lower molecular weight buffers are unsatisfactory because of their tendency to leak out of an encapsulating membrane. Methods of making such compositions are described, as well as a particular application in a fiber optic carbon dioxide physiological probe.

8 Claims, No Drawings

POLYMERIC BUFFERING COMPOSITION

This is a divisional of the prior application Ser. No. 07/813,276, filed on Dec. 23, 1991, now U.S. Pat. No. 5,298,645, of Lokanathan M. Iyer, Kenneth S. Lyon and Vince Brotherton for POLYMERIC BUFFERING COMPOSITION FOR FIBER-OPTIC PHYSIOLOGICAL PROBE AND METHOD OF MAKING THE SAME, the benefit of the filing date of which are hereby claimed under 35 U.S.C. § 120.

FIELD OF THE INVENTION

The present invention relates to chemical buffering compositions for fiber optic physiological probes and methods for making chemical buffering compositions, and more particularly, to chemical buffering compositions incorporated into a polymeric matrix for use with physiological probes.

BACKGROUND OF THE INVENTION

A buffer is generally a solution containing both a weak acid and its conjugate weak base whose pH changes only slightly on addition of acid or alkali. The weak acid becomes a buffer when alkali is added and the weak base becomes a buffer on addition of acid. This action can be explained by the reaction:

$$A + HOH \rightarrow B + H_3O_n \quad (1)$$

in which the base B is formed by the loss of proton from the corresponding acid A. The acid may be a cation such as $NH_4^+$, a neutral molecule such as $CH_3COOH$, or an anion such as $H_2PO_4^-$. When alkali is added, hydrogen ions are removed to form water, but as long as the added alkali is not in excess of the buffer acid, many of the hydrogen ions are replaced by further ionization of the acid to maintain the equilibrium. When acid is added, this reaction is reversed as hydrogen ions combine with the base to form acid.

Buffers of this type are used in many applications. One specific application is the use of a bicarbonate as a buffering composition in a fiber optic physiological probe, such as the one described in U.S. Pat. No. 4,925,268 issued May 15, 1990 and U.S. Pat. No. 5,000,901 issued Mar. 19, 1991. The probes described in these two patents include a carbon dioxide sensor that relies upon the optical absorbance of an indicator material, such as phenol red (PR) in its basic form, to provide a measure of carbon dioxide in the analyte. Generally, the degree that phenol red absorbs visible light is affected by the pH of the environment around the phenol red. As described below, in the carbon dioxide sensors of the noted patents, the pH of the environment around the phenol red is made dependent upon the concentration of carbon dioxide around the sensor, by relying upon a buffering composition. The buffering solution responds to changes in the concentration of carbon dioxide by changing the pH of the environment in which it is contained.

In the sensors described in the above-noted patents, the phenol red is codissolved in a matrix of methyl methacrylate (MMA), methacrylamidopropyltrimethylammonium chloride (MAPTAC), and polyethylene glycol (PEG) having a molecular weight of about 600K. The matrix also incorporates a base that establishes an equilibrium within the matrix, such that when the concentration of carbon dioxide in the matrix changes, the pH within the matrix changes. The change in pH affects the absorbance of phenol red. One type of buffer described in the above-noted patents comprises a bicarbonate ion. The bicarbonate ion is incorporated into the matrix in the form of an inorganic salt, such as a sodium salt. Bicarbonate sets up the following equilibrium that is sensitive to the carbon dioxide concentration:

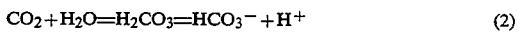

$$CO_2 + H_2O = H_2CO_3 = HCO_3^- + H^+ \quad (2)$$

In the probe described in the above-noted patents, a matrix of MMA/MAPTAC/PP/PEG is applied to the end of an optical fiber by using a solvent based film coating technique. The bicarbonate can then be introduced into the matrix by diffusion, so that a coating of the MMA/MAPTAC/PR/PEG matrix impregnated with sodium bicarbonate covers the end of the optical fiber. The sensor matrix can be further encapsulated by a layer of a plastic which forms a gas permeable, but ion impermeable membrane around the matrix. Visible light is directed onto the sensor matrix through the optical fiber. The absorbance of the impinging light by the phenol red can be measured by detecting the light reflected by the sensor matrix.

When the probe is designed to monitor carbon dioxide concentrations in blood, the accuracy of the measurement is vitally important. In the past, the possibility of bicarbonate ions leaking out of the sensor matrix increased the likelihood that signal drift would occur. Leaking of the bicarbonate ions from the sensor matrix could result if small voids occurred in the plastic membrane encapsulating the sensor matrix.

U.S. Pat. Nos. 5,000,901 and 4,925,268 teach that as an alternative to sodium bicarbonate, other bases having a pKa in the targeted physiological range can be used. Suitable monomeric bases that are listed include 2-vinylpyridine, 4-vinylpyridine, histamine, 1-vinylimidazole and 4-vinylimidazole. These patents note that the vinylic monomers can be homopolymerized or copolymerized to provide a polymeric base of sufficiently high molecular weight to nullify loss by permeation when physically entrained in the sensor matrix. In order to iramobilize the base by covalent linkage to the sensor matrix, the monomers are described as being copolymerizable with IAMA or otherwise bondable to a resin emulsion. The disclosed monomeric bases have a pKa that is near the low end of the physiological range and accordingly, compared to bicarbonate, they are not as effective at providing a sensor that has the desired sensitivity and response time. Accordingly, while the polymeric bases described above may avoid the potential problem of leakage of the base from the sensor matrix and the consequent signal drift, they are less desirable from an accuracy and speed standpoint.

The buffering composition formed in accordance with the present invention overcomes the problems of using tree bicarbonate ions as a buffer in a sensor matrix such as that described above to monitor carbon dioxide concentrations. The composition of the present invention avoids the potential leakage and signal drift problems associated with the use of free bicarbonate without a sacrifice in performance in demanding applications such as physiological probes.

SUMMARY OF THE INVENTION

In one aspect, the present invention is a buffering composition that comprises the following formula:

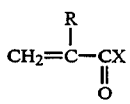
(3)

wherein R is hydrogen or methyl radical; and X is:

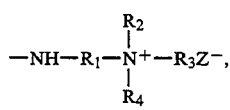
(4)

or

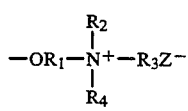
(5)

wherein $R_1$ is an alkyl or hydroxyalkyl group, $R_2$, $R_3$, and $R_4$ are hydrogen, alkyl or hydroxyalkyl, and $Z^-$ is bicarbonate.

In one embodiment of this aspect of the present invention, R is methyl radical, $R_1$ is propyl radical, and $R_2$, $R_3$, and $R_4$ are methyl radicals.

In another aspect, the present invention relates to a method for making methacrylamidopropyltrimethylarnmonium bicarbonate that includes passing methacrylamidopropyltrimethylammonium chloride over an ion exchange media that includes bicarbonate ions that are exchangeable with the chloride ions of the methacrylamidopropyltrimethylammonium chloride.

In another aspect, the present invention relates to a polymeric buffering composition that includes a copolymer of the buffering composition described above and a nonionic, hydrophobic acrylate having the formula:

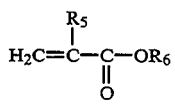
(6)

wherein $R_5$ is hydrogen or methyl radical and $R_6$ is methyl, ethyl, or butyl radical. One particular embodiment of this aspect of the present invention is a polymeric buffering composition wherein $R_1$ is propyl radical, and R, $R_2$, $R_3$, $R_4$, $R_5$, and $R_6$ are methyl radicals.

In still another aspect, the present invention relates to an indicator matrix for use in a carbon dioxide fiber optic physiological sensor that includes the polymeric buffering composition described above, and an indicator molecule capable of responding to an analyte of choice in an optically detectable manner. In one embodiment of this aspect of the present invention, the indicator molecule can be phenol red.

The foregoing aspects and many of the attendant advantages of this invention will become more readily appreciated as the same becomes better understood by reference to the following detailed description.

DETAILED DESCRIPTION OF THE PREFERRED EMBODIMENT

While the preferred embodiment of the invention has been illustrated and described, it will be appreciated that various changes can be made therein without departing from the spirit and scope of the invention.

The buffering composition formed in accordance with the present invention comprises the following formula:

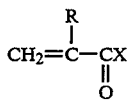
(3)

wherein R is hydrogen or methyl radical, and X is:

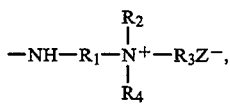
(4)

or

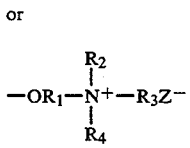
(5)

wherein $R_1$ is an alkyl or hydroxyalkyl group, $R_2$, $R_3$, and $R_4$ are hydrogen, alkyl, or hydroxyalkyl, and $Z^-$ is bicarbonate.

The bicarbonate ion is capable of acting as a buffering composition according to the following reaction:

$$CO_2 + H_2O \rightleftharpoons H_2CO_3 \rightleftharpoons HCO_3^- + H^+ \quad (2)$$

In this manner, the bicarbonate as described below in more detail, allows a fiber optic carbon dioxide sensor that incorporates a bicarbonate ion and an indicator molecule whose response is dependent upon the pH in the sensor's environment to provide a measure of carbon dioxide in that environment. For instance, if the concentration of the carbon dioxide increases, the equilibrium shifts toward the right side of Equation 2, and the concentration of $H^+$ increases, thus decreasing the pH. Conversely, if the concentration of carbon dioxide decreases the equilibrium shifts to the left and the $H^+$ concentration decreases, thus increasing the pH.

A specific example of a buffering composition formed in accordance with the present invention is methacrylamidopropyltrimethylammonium bicarbonate (hereinafter MAPTAB). MAPTAB can be represented by the formula:

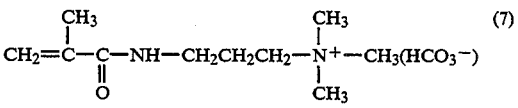
(7)

MAPTAB includes bicarbonate ions bound to the relatively large organic moiety. Since the bicarbonate ions are bound, they are less likely than free bicarbonate to leak from a polymeric matrix into which they are incorporated.

Applicants have discovered that MAPTAB can be produced by exchanging chloride ions on methacrylamidopropyltrimethylammonium chloride (MAPTAC) commercially available from Polysciences of Warrington, Pa. with bicarbonate ions. The exchange can surprisingly be accomplished by passing MAPTAC over an ion exchange media that includes bicarbonate ions that are exchangeable with the chloride ions. Passing the MAPTAC over the appropriate ion exchange resin causes the chloride ions of MAPTAC to be displaced and replaced by bicarbonate ions to provide MAPTAB. Applicants have found that such exchange could be accomplished despite the strong attraction between the ammonium group of MAPTAC and the chloride ions. A representative procedure for making MAPTAB is provided in Example 1.

In addition to passing a chloride containing precursor over an ion exchange media in the bicarbonate form, the buffering compositions of the present invention can be made using organic synthesis techniques.

One example of an ion exchange media that can be used to produce MAPTAB is a Rohm and Haas Company ion exchange resin available under the name Amberlite ® IRA-900C. The Amberlite ® IRA-900C resin is a styrenedivinylbenzene matrix in bicarbonate form. The resin has a wet density of about 1.07 grams/cubic centimeter. The effective size of the resin is about 0.50 millimeters. The total exchange capacity of the resin is approximately 1.0 milliequivalent/milliliter wet.

To provide a polymeric buffering composition, the MAPTAB described above can be co-polymerized with a non-ionic, hydrophobic acrylate represented by the formula:

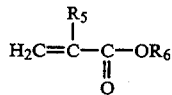

(6)

wherein $R_5$ is hydrogen or methyl radical and $R_6$ is methyl, ethyl or butyl radical. One specific example of such an acrylate is methylmethacrylate (MMA). The polymerization product of MAPTAB and MMA is particularly useful in physiological sensors such as those described in U.S. Pat. Nos. 4,925,268 and 5,000,901 because of good refractive index matching when used with plastic optical fibers having methylmethacrylate cores. Applicants have observed that when the polymeric buffering composition described above is incorporated into a fiber-optic carbon dioxide sensor formed in accordance with the patents noted above, the sensor is more stable with respect to a predetermined reference point, e.g., partial pressure of carbon dioxide, compared to sensors wherein the bicarbonate is diffused into a polymeric matrix.

The polymerization reaction can be performed in a variety of organic solvents. It is generally desirable, however, for the organic solvent to have some appreciable solubility in water. Water soluble organic acids and alcohols are thus particularly useful. Polymerization solvents that are especially preferred in the process are ethanol or acetic acid.

Reaction temperatures from about 55° to 80° C. can be used, with 75° C. being most preferable. Polymerization proceeds via a free-radical process, and any of the polymerization initiators conventionally utilized to form polymethylmethacrylates may be employed. One example of such a polymerization initiator is azo-bisisobutryonitrile (AIBN). The co-polymer can be prepared in bulk form by polymerizing the reaction mixture in a suitable closed vessel such as a stopped test tube. Example 2 illustrates the co-polymerization of MAPTAB and MMA.

In the particular embodiment where the MAPTAB/MMA co-polymer is to be used in a fiber optic physiological carbon dioxide sensor such as the ones described in the Background, the mixture that is co-polymerized is preferably about 60 to 80 weight % acrylate and 40 to 20 weight % nonacrylate. A preferred matrix includes about 94 mole % MMA and about 6 mole % MAPTAB.

The MAPTAB/MMA copolymer provides sites where water soluble indicator molecules can be covalently bonded to prevent their leakage from a sensor made from the copolymer. The copolymer also allows free egress of gaseous analytes such as carbon dioxide. The copolymer is hydrophilic; however, its hydrophilicity can be regulated to prevent undue swelling and the attendant risk of dissociation of the copolymer from the end of the fiber. For certain applications, the copolymer is also semipermeable, having minute openings or pores of a size large enough to permit passage of the targeted analyte substance, but sufficiently small so as to preclude passage of certain dissolved or colloidal substances that may interfere with the sensitivity of the indicator material.

An indicator matrix for use in a physiological probe can be provided from the copolymer of MAPTAB and MMA by incorporating an indicator molecule or material into the copolymer. Examples of suitable indicator materials for use in a carbon dioxide sensor include absorptive molecules such as phenol red or carboxynaphthophthalein (hydrogen ion analyte). The indicator molecule may also be a luminescent molecule, such as carboxynaphthofluorescein.

Phenol red can be incorporated into the MAPTAB/MMA copolymer by either admixing it into the copolymer or by covalently bonding the phenol red to the MAPTAB/MMA copolymer through an aminoarylakylamine. When phenol red is admixed in the MAPTAB/MMA copolymer, it can be incorporated in the form a sodium salt. A representative protocol for admixing phenol red into a MAPTAB/MMA copolymer is set forth in Example 3. If the phenol red is to be covalently bonded to the MAPTAB/MMA copolymer, it is generally preferred to introduce the aminoarylakylamines to the copolymer before reaction of the phenol red with the aminoaryakylamine. A representative protocol for covalently bonding phenol red to the MAPTAB/MM A copolymer is set forth in Example 4.

The buffering composition, polymeric buffering composition, and the indicator matrix formed in accordance with the present invention are useful in carbon dioxide optical physiological probes that include sensing mediums that include indicator materials sensitive to pH. Specific examples of such sensors are described in U.S. Pat. Nos. 4,925,260 and 5,000,901. Naturally, other carbon dioxide sensors operating on similar principles could benefit from the advantages provided by the compositions and methods of the present invention.

The following Examples are provided to illustrate the advantages and to assist one ordinary skill in making and using the invention. The Examples are not intended in any way to otherwise limit the scope of the disclosure and the protection granted by Letters Patent hereon.

EXAMPLE 1

Preparation of MAPTAB

Methacrylamidopropyltrimethylammonium chloride (MAPTAC) was obtained from Polysciences of Warrington, Pa. A 30 centimeter tall glass chromatography column having a 2.5 centimeter diameter was packed using a double distilled water slurry of Rohm and Haas Amberlite® IRA 900C ($HCO_3^-$ form). The packed column height was 28 centimeters. Excess water was allowed to drain from the column until the water level reached the column face. A 500 milliliter separatory funnel, containing 300 milliliters of MAPTAC was attached to the column, and the MAPTAC was introduced into the column dropwise, allowing the solution to drain from the bottom of the column, where fractions were collected. Fifty milliliter fractions were collected after allowing the first 150 milliliters of water to drain from the column. The fractions were analyzed using a Haake Buchler Chloridometer (coulometric titrator of $Cl^-$) The amount of chloride on the organic moiety of MAPTAC was reduced one hundred-fold after passing over the column. The average chloride content of MAPTAC determined by coulometric titration is 400 milliequivalents per liter. The collected fractions from the column averaged four milliequivalents per liter.

EXAMPLE 2

Synthesis of MAPTAB/MMA Copolymer

Methyl methacrylate (MMA) was obtained from Polysciences of Warrington, Pa.

A mixture of 6.65 milliliters of MMA monomer purified by distillation, 1.7 milliliters of 50 weight % aqueous methacrylamidopropyltrimethylammonium bicarbonate (MAPTAB) produced by the method of Example 1, 4.0 milliliters of ethanol and 30 milligrams of 2, 2'-azobisisobutyronitrile (AIBN) from Polysciences were stored in a sealed vial at 75° C. for 24 hours. The resulting 94 mole % MMA and 6 mole % MAPTAB copolymer was removed and a solution of the copolymer prepared by dissolving 5.0 grams of the copolymer in 50 milliliters of ethanol over several hours. The solution was purified by ultrafiltering the copolymer solution through an ultrafiltration membrane (100K MWCO). The retentate was collected, stripped of solvent, and the solid dissolved in 2-methoxyethanol at 13% solids weight/weight.

EXAMPLE 3

Preparation of Indicator Matrix With Admixed Phenol Red

A solution of polyethylene oxide having a molecular weight of 600K was formed by dissolving 1.0 grams of solid polyethylene oxide 600K in 19 grams of 2-methoxyethanol (5% weight/weight) and stirred or sonicated until homogenous. A solution of MAPTAB/MMA copolymer according to Example 2 was prepared by dissolving 1.0 grams of solid copolymer in 6.7 grams of 2-methoxyethanol (13% weight/weight) and stirred until homogenous. 3.07 grams of the 13% weight/weight solution of MAPTAB/MMA copolymer was mixed with 2.0 grams of the 5% weight/weight polyethylene oxide 600K solution. The ratio of solid MAPTAB/MMA copolymer to solid polyethylene oxide 600K was 80% to 20%. This solution was stirred until homogenous. 0.005 grams of phenol red were then added to the solution, which was stirred until homogenous. This solution could then can be applied to the end of an optical fiber by film-coating techniques to provide a carbon dioxide sensor.

EXAMPLE 4

Preparation of Indicator Matrix With Phenol Red Covalently Bound 4-(aminophenyl)-ethylamine (hereinafter APE) i s purified as the dihydrochloride by taking 4.0 grams of APE from Aldrich Chemical Company, Inc., Milwaukee, Wis. in 8 milliliters of concentrated hydrochloric acid at 0° C. and recrystallizing the dihydrochloride from water-ethanol (100 milliliters of 95:5 water-ethanol).

Two milliliters of the thirteen percent solids weight/weight MAPTAB/MMA solution from Example 2 are azeotroped with anhydrous ethanol (3×50 milliliters) and redissolved in 25 milliliters of anhydrous ethanol. 0.83 grams of the APE-dihydrochloride and one milliliter of freshly distilled triethylamine (Aldrich) as a catalyst are added, and the solution stirred in an oven at 55° C. for 48 hours. The solvent and excess triethylamine are removed on a rotary evaporator.

The MAPTAB/MMA/APE reaction product is dissolved in 20 milliliters of denatured ethanol at 0° C. and to that solution is added three milliliters of concentrated hydrochloric acid and three milliliters of water. A solution of 0.3 grams of sodium nitrite in two milliliters of water is then added, and the resulting solution is stirred at 0° C. for three hours. This mixture is then added to a solution of 2.4 grams of phenol red (sodium salt of phenol red; Aldrich), 2.5 grams of potassium bicarbonate in 30 milliliters of water, and 30 milliliters of denatured ethyl alcohol, while stirring at 0° C. It is important, when coupling the diazotized APE polymer to phenol red, to maintain the pH at about 8.5 using potassium bicarbonate, use excess phenol red to saturate all diazotized sites, and prevent diazonium hydroxide/phenol formation. The resulting solution is stirred over several hours at 0° C.

The resulting orange-red solution from the coupling reaction is brought to a pH of 1 with concentrated hydrochloric acid at 0° C., and 500 milliliters of ice cold water is added. The product is filtered, and the residue is washed with water (3 times with 100 milliliters).

The crude product is mixed with 2.5 grams of potassium bicarbonate in 250 milliliters water, and a stirred cell separation is conducted using a type F membrane (Spectrum Ultrapor, Type F MWCO: 50,000; Spectrum Medical Industries, Los Angeles, Calif.) under nitrogen gas. The ultrafiltration is continued until the filtrate is colorless, as indicated by nonabsorption at 570 nanometers. The reddish-brown pure product is dried in a desiccator. The resulting product is a MAPTAB/MMA/APE matrix with phenol red covalently bound thereto.

While the present invention has been described in conjunction with a preferred embodiment, one of ordinary skill, after reading the foregoing specification, will be able to effect various changes, substitutions of equivalents, and alterations to the methods and compositions set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. A polymeric buffering composition comprising a copolymer of a buffering composition represented by the formula:

$$CH_2=\underset{\underset{O}{\|}}{\overset{R}{\underset{|}{C}}}-CX \quad (3)$$

wherein R is hydrogen or methyl radical, and X is:

$$-NH-R_1-\underset{\underset{R_4}{|}}{\overset{R_2}{\overset{|}{N^+}}}-R_3Z^-, \quad (4)$$

or $$-OR_1-\underset{\underset{R_4}{|}}{\overset{R_2}{\overset{|}{N^+}}}-R_3Z^- \quad (5)$$

wherein
$R_1$ is an alkyl or hydroxyalkyl group,
$R_2$, $R_3$, and $R_4$ are hydrogen, alkyl, or hydroxyalkyl, and
$Z^-$ is bicarbonate; and
a non-ionic, hydrophobic acrylate represented by the formula:

$$H_2C=\underset{\underset{O}{\|}}{\overset{R_5}{\underset{|}{C}}}-C-OR_6 \quad (6)$$

wherein
$R_5$ is hydrogen or methyl radical and $R_6$ is methyl, ethyl, or butyl radical.

2. The buffering composition of claim 1, wherein R is methyl radical, $R_1$ is propyl radical, and $R_2$, $R_3$, and $R_4$ are methyl radicals.

3. The buffering composition of claim 1, wherein $R_5$ and $R_6$ are methyl radicals.

4. An indicator matrix for use in a fiber-optic sensor suitable for monitoring physiological analyte concentration comprising:

a copolymer of a buffering composition represented by the formula:

$$CH_2=\underset{\underset{O}{\|}}{\overset{R}{\underset{|}{C}}}-CX \quad (3)$$

wherein R is hydrogen or methyl radical, and X is:

$$-NH-R_1-\underset{\underset{R_4}{|}}{\overset{R_2}{\overset{|}{N^+}}}-R_3Z^-, \quad (4)$$

or $$-OR_1-\underset{\underset{R_4}{|}}{\overset{R_2}{\overset{|}{N^+}}}-R_3Z^- \quad (5)$$

wherein
$R_1$ is an alkyl or hydroxyalkyl group,
$R_2$, $R_3$, and $R_4$ are hydrogen, alkyl, or hydroxyalkyl, and
$Z^-$ is bicarbonate; and
a non-ionic, hydrophobic acrylate represented by the formula:

$$H_2C=\underset{\underset{O}{\|}}{\overset{R_5}{\underset{|}{C}}}-C-OR_6 \quad (6)$$

wherein
$R_5$ is hydrogen or methyl radical and $R_6$ is methyl, ethyl, or butyl radical; and
an indicator molecule capable of responding to the analyte in an optically detectable manner.

5. The indicator matrix of claim 4, wherein R is methyl radical, $R_1$ is propyl radical, and $R_2$, $R_3$, and $R_4$ are methyl radicals.

6. The indicator matrix of claim 4, wherein $R_5$ and $R_6$ are methyl radicals.

7. The indicator matrix of claim 4, wherein the indicator molecule is phenol red.

8. The indicator matrix of claim 4, wherein the analyte is carbon dioxide.

* * * * *

UNITED STATES PATENT AND TRADEMARK OFFICE
CERTIFICATE OF CORRECTION

PATENT NO. : 5,376,306
DATED : December 27, 1994
INVENTOR(S) : L.M. Iyer et al.

It is certified that error appears in the above-indentified patent and that said Letters Patent is hereby corrected as shown below:

| COLUMN | LINE | |
|---|---|---|
| 2 | 46 | "iramobilize" should read --immobilize-- |
| 2 | 48 | "IAMA" should read --MMA-- |
| 2 | 62 | "tree" should read --free-- |
| 3 | 33-34 | "methacrylamidopropyltrimethylarnmonium" should read --methacrylamidopropyltrimethylammonium-- |
| 8 | | "i s" should read --is-- |

Signed and Sealed this

Eleventh Day of April, 1995

Attest:

BRUCE LEHMAN

Attesting Officer     Commissioner of Patents and Trademarks